(12) United States Patent
Zeijlemaker

(10) Patent No.: US 9,549,688 B2
(45) Date of Patent: Jan. 24, 2017

(54) IMPLANTABLE MEDICAL DEVICE DETECTION

(75) Inventor: Volkert A. Zeijlemaker, Landgraaf (NL)

(73) Assignee: Medtronic, Inc., Minneapolis, MN (US)

(*) Notice: Subject to any disclaimer, the term of this patent is extended or adjusted under 35 U.S.C. 154(b) by 1492 days.

(21) Appl. No.: 11/379,847

(22) Filed: Apr. 24, 2006

(65) Prior Publication Data

US 2007/0265685 A1 Nov. 15, 2007

(51) Int. Cl.
| | |
|---|---|
| A61B 5/06 | (2006.01) |
| A61B 5/00 | (2006.01) |
| A61B 5/055 | (2006.01) |
| A61N 1/37 | (2006.01) |
| A61N 1/372 | (2006.01) |
| G01R 33/28 | (2006.01) |
| A61N 1/08 | (2006.01) |
| G01R 33/36 | (2006.01) |

(52) U.S. Cl.
CPC .............. *A61B 5/06* (2013.01); *A61B 5/0031* (2013.01); *A61B 5/055* (2013.01); *A61N 1/37* (2013.01); *A61N 1/37258* (2013.01); *G01R 33/287* (2013.01); *A61N 1/08* (2013.01); *A61N 1/3718* (2013.01); *G01R 33/288* (2013.01); *G01R 33/3692* (2013.01)

(58) Field of Classification Search
None
See application file for complete search history.

(56) References Cited

U.S. PATENT DOCUMENTS

| | | | | |
|---|---|---|---|---|
| 5,438,990 | A * | 8/1995 | Wahlstrand et al. | 324/260 |
| 5,694,952 | A * | 12/1997 | Lidman et al. | 128/899 |
| 5,697,958 | A * | 12/1997 | Paul et al. | 607/31 |
| 6,073,049 | A * | 6/2000 | Alt et al. | 607/31 |
| 6,194,898 | B1 * | 2/2001 | Magnuson et al. | 324/300 |
| 6,402,689 | B1 * | 6/2002 | Scarantino et al. | 600/300 |
| 6,482,154 | B1 * | 11/2002 | Haubrich et al. | 600/300 |
| 6,580,947 | B1 * | 6/2003 | Thompson | 607/30 |
| 6,963,779 | B1 * | 11/2005 | Shankar | 607/30 |
| 7,561,915 | B1 | 7/2009 | Cooke et al. | |
| 2002/0026223 | A1 * | 2/2002 | Riff et al. | 607/27 |
| 2003/0083570 | A1 | 5/2003 | Cho et al. | |
| 2004/0167587 | A1 * | 8/2004 | Thompson | 607/60 |
| 2005/0021108 | A1 | 1/2005 | Klosterman et al. | |
| 2005/0070786 | A1 * | 3/2005 | Zeijlemaker et al. | 600/411 |
| 2005/0070975 | A1 * | 3/2005 | Zeijlemaker et al. | 607/60 |
| 2005/0113876 | A1 * | 5/2005 | Weiner et al. | 607/36 |
| 2005/0225327 | A1 | 10/2005 | Maschke | |
| 2006/0025820 | A1 * | 2/2006 | Phillips et al. | 607/2 |
| 2009/0138058 | A1 * | 5/2009 | Cooke et al. | 607/5 |

FOREIGN PATENT DOCUMENTS

| | | |
|---|---|---|
| WO | WO2005035048 A | 4/2005 |
| WO | WO9641203 A | 8/2007 |

OTHER PUBLICATIONS

Baker et al. Evaluation of Specific Absorption Rate as a Dosimeter of MRI-Related Implant Heating, 2004, JMRI, 20:315-320.*

* cited by examiner

*Primary Examiner* — Bo J Peng

(57) ABSTRACT

A detection unit and a method for detecting an implanted medical device in an MRI environment employ a telemetry transmission from the implanted medical device.

20 Claims, 3 Drawing Sheets

IMPLANTABLE MEDICAL DEVICE DETECTION

FIELD OF THE INVENTION

The present invention pertains to implantable medical devices and more particularly to detecting these devices in a magnetic resonance imaging (MRI) environment.

BACKGROUND

Many implantable medical devices (IMD's), for example, including pacemakers, cardioverter-defibrillators and neural stimulators, are operatively coupled to electrodes, which are joined to elongate lead wires that extend from the devices to a target site either on or within a body of a patient. The electrodes sense electrical signals from the patient, for example cardiac depolarization signals, which are used to diagnose the patient and, in many cases, may be used to guide or dictate therapy delivery. Having such an IMD may be a contraindication for MRI, due, at least in part, to the lead wires acting as antennae, which pick up radio-frequency (RF) energy transmitted during MRI; the RF energy can cause heating of the electrodes, which are coupled to the lead wires, and may introduce sensing artifact, causing erroneous cardiac event detection that can compromise therapy delivery during MRI. Thus, there is a need to detect if a patient has an IMD before allowing the patient to undergo MRI.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
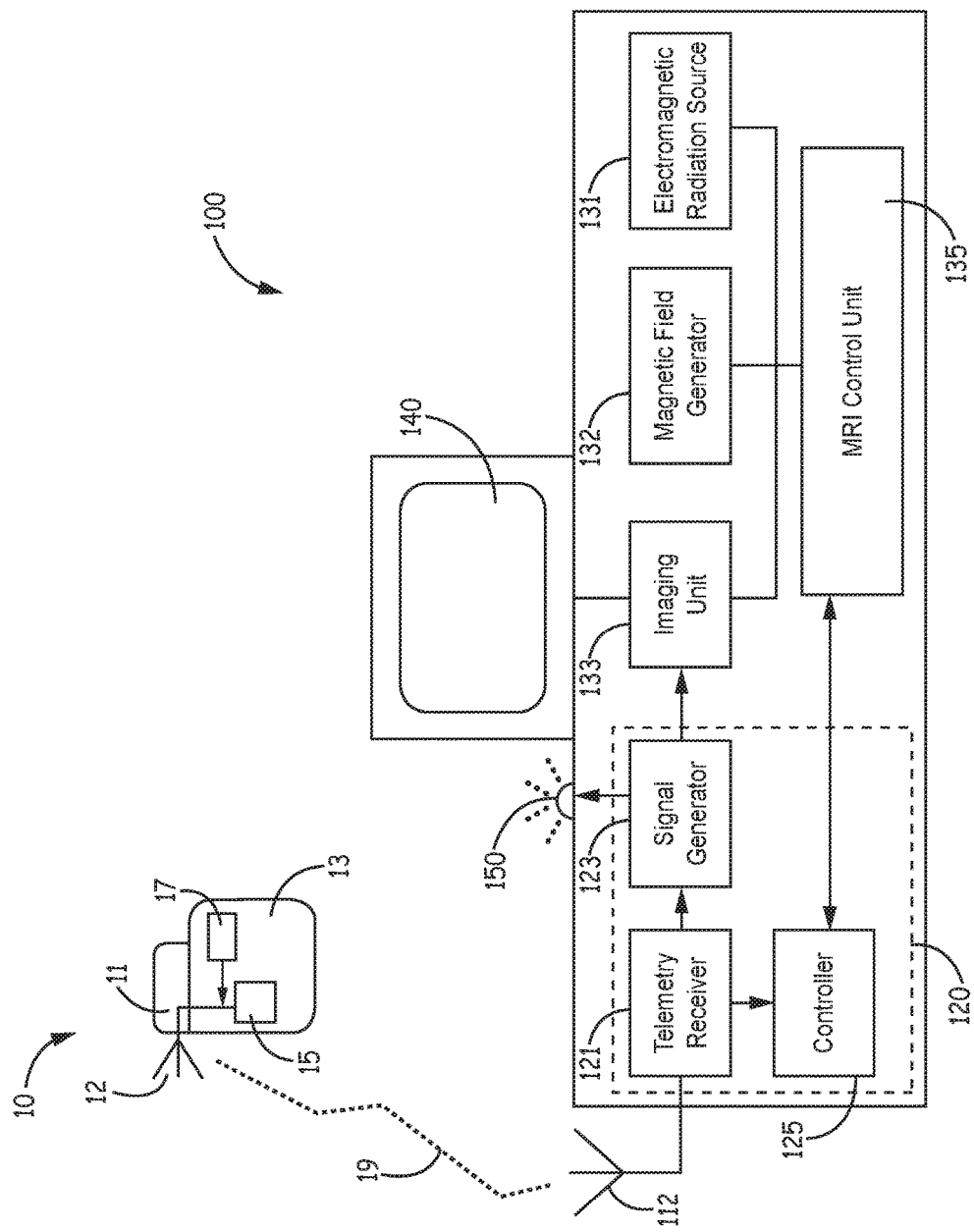
FIG. 1 is a schematic block diagram of a system, according to some embodiments of the present invention.

FIG. 1 is a schematic block diagram of a system according to some embodiments of the present invention. FIG. 1 illustrates an IMD 10 in the presence of an MRI system 100. Although not shown as such, it should be appreciated that IMD 10 is implanted within a body of a patient who has been referred for diagnostic imaging, via MRI system 100; thus, apart from the methods and apparatus of the present invention, an MRI operator may not be aware of IMD 10. FIG. 1 further illustrates IMD 10 including a can or housing 13, which encloses a battery and electronic components, and, coupled to housing 13, a connector header 11, which houses a telemetry antenna 12 and connections for electrical leads, which are not shown, but are understood to be components of IMD 10. Some of the salient electronic components are shown schematically and include a telemetry unit 15 and a telemetry activation module 17; according to the illustrated embodiment, particular telemetry signals 19 of a prescribed frequency or frequencies are sent from unit 15 via antenna 12 when activation module 17 detects the presence of a static magnetic field of a strength associated with MRI. According to some embodiments activation module 17 includes a reed switch which closes in the presence of the static magnetic field in order to couple unit 15 to antenna 12; according to other embodiments, activation module 17 includes a Hall effect sensor that detects the static magnetic field to activate unit 15 for transmission of telemetry signals 19. Those skilled in the art will appreciate that antenna 12 is shown schematically and is coupled, along with lead connectors of connector header 11, via feedthroughs extending through housing 13 to the electronic components housed therein.

MRI system 100 is shown including a telemetry antenna 112 coupled to a telemetry receiver 121, which is part of an IMD detection unit 120; detection unit 120 scans the frequency band for possible IMD transmissions and antenna 112 is tuned to receive the particular frequencies of transmission 19. According to some embodiments, receiver 121 may include transmitter capability, which would allow detection unit 120 to send an activation signal, different from the static magnetic field of system 100 that activates transmission 19. FIG. 1 further illustrates detection unit 120 including a signal generator 123 coupled to receiver 121; according to the illustrated embodiment, signal generator 123 sends a signal, indicating the presence of IMD 10, to a signaling element 150 and/or to a monitor 140 of system 100 via imaging unit 133. According to some embodiments, element 150 provides a visible signal, for example a flashing light; according to alternate embodiments, element 150 provides an audible alarm. In some embodiments, IMD 10 may further transmit additional information, carried by transmission 19, concerning IMD 10 to detection unit 120. The received signal may pass through signal generator 123 and imaging unit 133 to monitor 140 for display, which may be useful, if MRI is still undertaken, to manage interactions between MRI and IMD 10; some examples of the additional information include, but are not limited to, information concerning the identity of the IMD type, the particular identity of IMD 10 (i.e. manufacturer and model number), special instructions for monitoring IMD 10, and programmed parameters of IMD 10.

FIG. 1 further illustrates detection unit 120 including a controller 125 coupled to receiver 121. According to the illustrated embodiment, controller 125 is coupled to an MRI control unit 135 in order to send control signals to unit 135 that cause unit 135 to alter the function of MRI system 100 according to the presence of IMD 10 as detected by receiver 121. According to some embodiments, MRI function may be altered by disabling a magnetic field generator 132 and an electromagnetic radiation source 131, which basically prevents scanning of the patient having IMD 10. According to an alternate embodiment, a low Specific Absorption Rate (SAR) scanning mode is activated by controller 125 to reduce an applied power of MRI system 100 and thereby prevent excessive heating of the electrodes via the electrical leads that would be coupled to IMD 10 and act as antennas. According to further embodiments, transmission 19 includes cardiac event signals from IMD 10, and controller 125 activates a scanning procedure that is synchronized with cardiac events so that MRI induced signals received by the leads coupled to IMD 10 are not misconstrued by IMD 10 as cardiac events.

Figure 2:
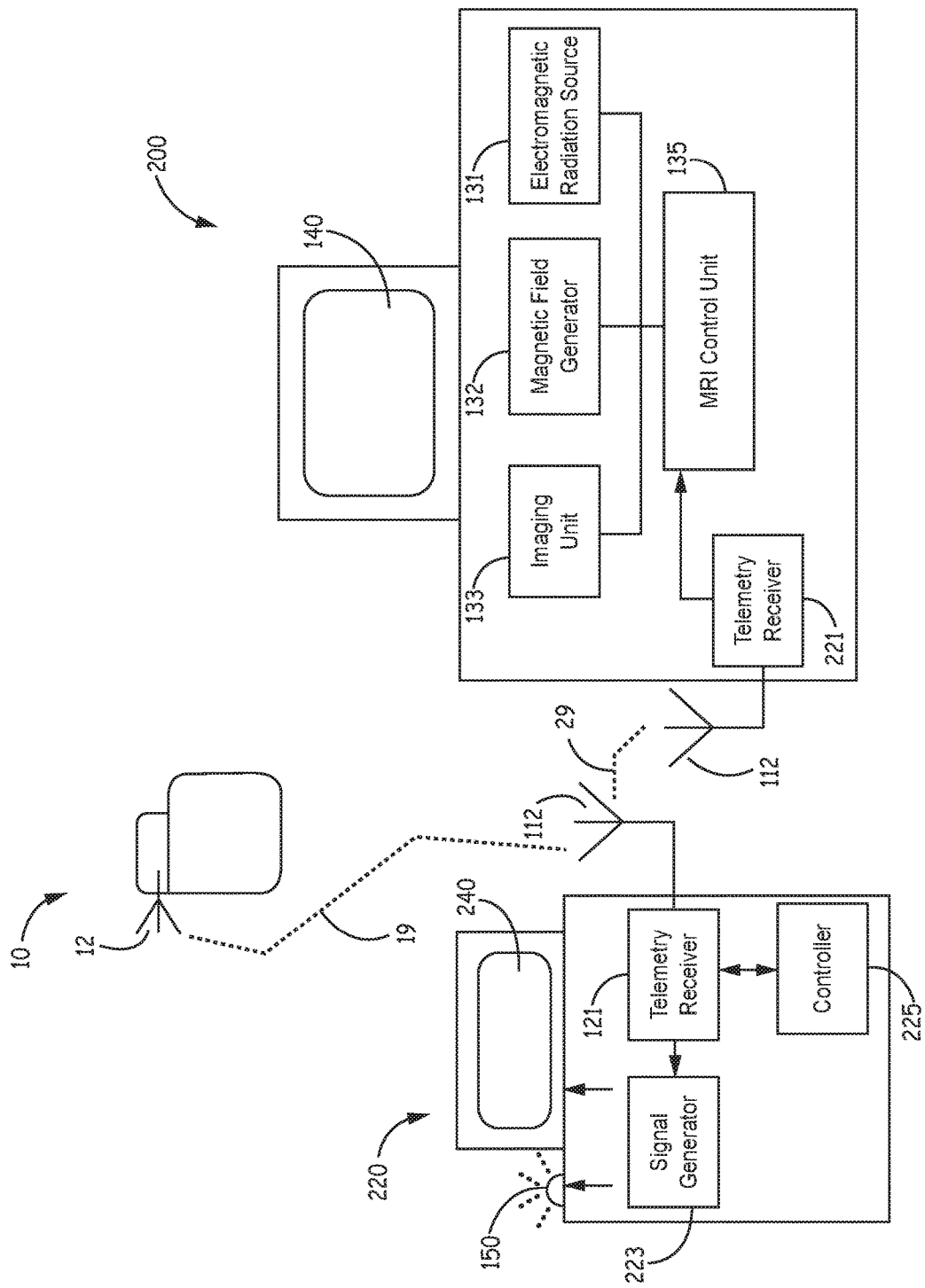
FIG. 2 is a schematic block diagram of a system, according to some alternate embodiments of the present invention.

It should be noted that some embodiments of the present invention include an IMD detection unit, which is kept in an MRI environment but is not hardwired into the MRI system; one such embodiment is described in conjunction with FIG. 2. FIG. 2 is a schematic block diagram of a system, according to some alternate embodiments of the present invention. FIG. 2 illustrates IMD 10 in the presence of an MRI system 200 and an IMD detection unit 220, which is similar to unit 120 illustrated in FIG. 1 but is packaged independently of an MRI system, i.e. system 200. According to some embodiments, detection unit 220 may be a handheld device equipped to detect the presence of IMD 10, via telemetry transmission 19 picked up by antenna 112 and receiver 121, as previously described. FIG. 2 further illustrates detection unit 220 including a signal generator 223 coupled to receiver 121, so that signal generator 223 may send a signal indicating the presence of IMD 10 to signaling element 150 and/or a monitor 240; types of signals, via element 150, and additional information, for example, displayed on monitor 240, are the same as those described in conjunction with FIG. 1.

FIG. 2 further illustrates detection unit 220 including a controller 225, which communicates with MRI system 200 via a telemetry transmission 29; according to the illustrated embodiment, receiver 121 further includes transmission capability to send transmission 29 to antenna 212 coupled to telemetry receiver 221 of MRI system 200. Controller 225 may thus send control signals to MRI control unit 135 that cause unit 135 to alter the function of MRI system 200 according to the presence of IMD 10 as previously described in conjunction with FIG. 1. It should be noted that, according to alternate embodiments, detection unit 220 does not include controller 225 and need not include both signaling element 150 and monitor 240, either being sufficient to inform an operator of system 200 that IMD 10 is present.

Figure 3:
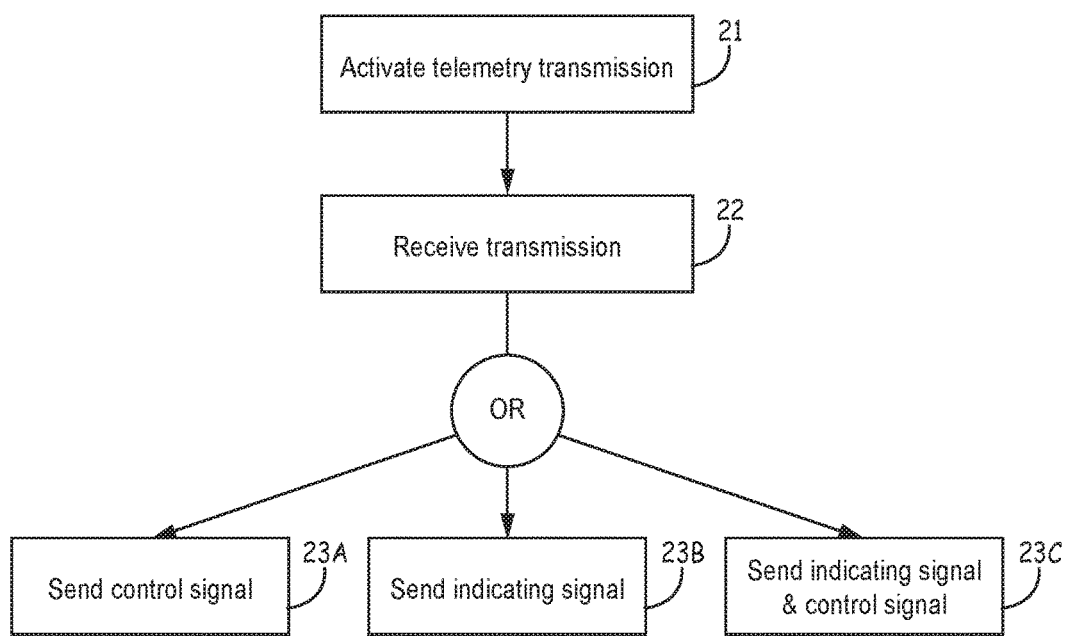
FIG. 3 is a flow chart outlining some methods of the present invention.

FIG. 3 is a flow chart outlining some methods of the present invention. FIG. 3 illustrates an initial step 21 in which telemetry transmission from an IMD is activated, for example, by a static magnetic field produced by an MRI system. According to some embodiments of the present invention, for example as illustrated in FIG. 1, a detection unit, hardwired into the MRI system, includes a telemetry receiver having an antenna tuned to the particular frequency assigned to the transmission, and, according to step 22, the transmission is received by the receiver. According to alternate methods outlined in FIG. 3, once the transmission is received, either a control signal is sent (step 23A) to automatically alter function of the MRI system due to the presence of the IMD, or an indicating signal is sent (23B) to a signaling element, which lets an operator of the MRI system know of the presence of the IMD, or both signals are sent (step 23C). Thus, a detection unit of the present invention may include one or both of signal generator 123 and controller 125 (FIG. 1), either being sufficient acting alone to prevent an operation of an MRI system that is incompatible with the IMD which is detected. Although FIG. 1 illustrates detection unit 120 hardwired into MRI system 100, the invention is not so limited and alternate embodiments include detection units that communicate wirelessly with other units of system 100.

In the foregoing detailed description, the invention has been described with reference to specific embodiments. However, it may be appreciated that various modifications and changes can be made without departing from the scope of the invention as set forth in the appended claims.

The invention claimed is:

1. A system comprising:
 an implanted medical device;
 an implantable medical device detection unit comprising:
  a receiver adapted to receive a telemetry transmission from the implanted medical device;
  a signal generator coupled to the receiver; and
  a signaling element coupled to the signal generator, wherein the signaling element includes a light, wherein the signal generator is configured to send a signal to the signaling element, responsive to receipt of the telemetry transmission received from the implanted medical device, to cause the light to illuminate to alert an MRI system operator of the presence of the implanted medical device; and
 an MRI system separate from the implantable medical device detection unit, wherein the MRI system is configured to wirelessly communicate with the implantable medical device detection unit.

2. The system of claim 1, wherein the signaling element further comprises an audible signaling element that provides an audible alarm alerting the MRI system operator of the presence of the implanted medical device.

3. The system of claim 1, wherein the implantable medical device detection unit further comprises a transmitter adapted to transmit an activation signal to the implanted medical device thereby activating the telemetry transmission from the implanted medical device.

4. The system of claim 3, wherein the transmitter is adapted to transmit the activation signal to the implanted medical device prior to activating a scanning procedure.

5. The system of claim 1, wherein the implantable medical device detection unit further comprises a monitor and wherein a message is displayed on the monitor for an MRI system operator.

6. The system of claim 5, wherein the message includes instructions for monitoring the medical device.

7. The system of claim 5, wherein the telemetry transmission includes information concerning a manufacturer and a model of the medical device, and the message displayed on the monitor includes the information concerning the manufacturer and model of the medical device.

8. The system of claim 1, wherein the telemetry transmission includes information concerning programmed parameters of the medical device, and the message displayed on the monitor includes the information concerning the programmed parameters of the medical device.

9. The system of claim 1, wherein the signal sent by the signal generator causes the light to flash to alert the MRI system operator that the implanted medical device is present.

10. The system of claim 1, wherein the signal generator is configured to send the signal to the signaling element to indicate the presence of the implanted medical device prior to scanning a patient having the implanted medical device.

11. The system of claim 1, wherein the MRI system further comprises:
 a magnetic field generator;
 an electromagnetic radiation source; and
 an MRI control unit adapted to alter the function of the MRI system by disabling one of the magnetic field generator or the electromagnetic radiation source in response to a control signal received from the implantable medical device detection unit.

12. A handheld device for detecting presence of an implantable medical device comprising:
- a receiver adapted to receive a telemetry transmission from an implanted medical device;
- a signal generator coupled to the receiver;
- a signaling element coupled to the signal generator, wherein the signaling element includes a light; and
- a device housing that encloses the receiver, the signaling element, and the signal generator, and is configured to be handheld,
- wherein the signal generator is configured to send a signal to the signaling element, responsive to receipt of the telemetry transmission received from the implanted medical device, to cause the light to illuminate to alert an MRI system operator of the presence of the implanted medical device.

13. The handheld device of claim 12, wherein the signal from the signal generator causes the light to flash to alert the MRI system operator of the presence of the implanted medical device.

14. The handheld device of claim 12, wherein the signaling element further comprises an audible signaling element that provides an audible alarm alerting the MRI system operator of the presence of the implanted medical device.

15. The handheld device of claim 12, further comprising a transmitter adapted to wirelessly transmit an activation signal to the implanted medical device thereby activating the telemetry transmission from the implanted medical device.

16. The handheld device of claim 12, further comprising:
- a transmitter adapted to wirelessly transmit a telemetry transmission to an MRI system; and
- a controller, wherein the controller is adapted to control the transmitter to send control signals to the MRI system to alter the function of MRI system in response to receiving the telemetry transmission from the implanted medical device.

17. The handheld device of claim 12, further comprising a monitor, wherein the signal generator is configured to display a message on the monitor for an MRI system operator.

18. The handheld device of claim 17, wherein the message includes information concerning programmed parameters of the implantable medical device.

19. The handheld device of claim 17, wherein the message includes information concerning a manufacturer and a model of the implantable medical device.

20. The handheld device of claim 12, wherein the signal generator is configured to send the signal to the signaling element to indicate the presence of the implanted medical device prior to scanning a patient having the implanted medical device.

* * * * *